United States Patent
Larsen

(10) Patent No.: US 9,468,373 B2
(45) Date of Patent: Oct. 18, 2016

(54) GAZE TRACKING VARIATIONS USING DYNAMIC LIGHTING POSITION

(71) Applicant: Sony Computer Entertainment Inc., Tokyo (JP)

(72) Inventor: Eric J. Larsen, Pacifica, CA (US)

(73) Assignee: Sony Interactive Entertainment Inc., Tokyo (JP)

( * ) Notice: Subject to any disclaimer, the term of this patent is extended or adjusted under 35 U.S.C. 154(b) by 0 days.

(21) Appl. No.: 14/493,723

(22) Filed: Sep. 23, 2014

(65) Prior Publication Data

US 2015/0085250 A1    Mar. 26, 2015

Related U.S. Application Data

(60) Provisional application No. 61/881,656, filed on Sep. 24, 2013.

(51) Int. Cl.
| | | |
|---|---|---|
| *A61B 3/14* | (2006.01) | |
| *A61B 3/10* | (2006.01) | |
| *A61B 3/00* | (2006.01) | |
| *A61B 3/113* | (2006.01) | |
| *G06K 9/00* | (2006.01) | |

(52) U.S. Cl.
CPC .............. *A61B 3/113* (2013.01); *A61B 3/14* (2013.01); *G06K 9/00604* (2013.01)

(58) Field of Classification Search
USPC ................................. 351/200–246
See application file for complete search history.

(56) References Cited

U.S. PATENT DOCUMENTS

| | | |
|---|---|---|
| 5,016,282 A | 5/1991 | Tomono et al. |
| 7,922,330 B2 * | 4/2011 | Van Saarloos ......... A61B 3/113 351/210 |
| 2002/0051116 A1 * | 5/2002 | Van Saarloos ......... A61B 3/113 351/204 |
| 2005/0100191 A1 | 5/2005 | Harbach et al. |
| 2008/0186449 A1 | 8/2008 | Sur et al. |
| 2009/0196460 A1 | 8/2009 | Jakobs et al. |
| 2010/0039618 A1 | 2/2010 | Lemos |
| 2010/0292676 A1 | 11/2010 | Larsen |
| 2011/0006978 A1 | 1/2011 | Yuan |
| 2011/0069277 A1 | 3/2011 | Blixt et al. |
| 2011/0109880 A1 * | 5/2011 | Nummela ............... A61B 3/113 351/210 |
| 2012/0086801 A1 | 4/2012 | Larsen |
| 2012/0105486 A1 | 5/2012 | Lankford et al. |
| 2012/0155703 A1 | 6/2012 | Hernandez-Abrego et al. |
| 2012/0257035 A1 | 10/2012 | Larsen |
| 2013/0096863 A1 | 4/2013 | Liu et al. |
| 2013/0321265 A1 * | 12/2013 | Bychkov ................. G06F 3/013 345/156 |

(Continued)

OTHER PUBLICATIONS

International Search Report and Written Opinion for International Application No. PCT/US2014/056998, dated Dec. 18, 2014.

(Continued)

*Primary Examiner* — Mohammed Hasan
(74) *Attorney, Agent, or Firm* — Joshua D. Isenberg; JDI Patent

(57) ABSTRACT

Aspects of the present disclosure relate to eye tracking systems and methods which track eyes by illuminating the eyes using a light source and detecting the eye illuminations using a sensor. Implementations of the present disclosure may utilize a light source with a dynamic lighting position to account for changes in lighting conditions during the tracking which interfere with detection of the eye illuminations, such as reflections in glasses which may obscure a user's eyes.

20 Claims, 4 Drawing Sheets

(56) References Cited

U.S. PATENT DOCUMENTS

| | | | |
|---|---|---|---|
| 2014/0055747 A1 | 2/2014 | Nistico et al. | |
| 2014/0168401 A1* | 6/2014 | De Bruijn | G06F 3/013 348/78 |
| 2014/0247232 A1 | 9/2014 | George-Svahn et al. | |
| 2015/0208019 A1* | 7/2015 | Stewart | G06F 3/0304 348/745 |

OTHER PUBLICATIONS

International Search Report and Written Opinion for International Application No. PCT/US2014/057003, dated Dec. 4, 2014.
International Search Report and Written Opinion for International Application No. PCT/US2014/057006, dated Jan. 22, 2015.
U.S. Appl. No. 14/493,738, to Eric J. Larsen, filed Sep. 23, 2014.
U.S. Appl. No. 14/493,766, to Eric J. Larsen, filed Sep. 23, 2014.
U.S. Appl. No. 61/881,656, to Eric J. Larsen, filed Sep. 24, 2013.
U.S. Appl. No. 61/881,660, to Eric J. Larsen, filed Sep. 24, 2013.
U.S. Appl. No. 61/881,662, to Eric J. Larsen, filed Sep. 24, 2013.
Non-Final Office Action for U.S. Appl. No. 14/493,766, dated Dec. 24, 2015.
Non-Final Office Action for U.S. Appl. No. 14/493,738, dated Jun. 6, 2016.
Non-Final Office Action for U.S. Appl. No. 14/493,766, dated May 26, 2016.

* cited by examiner

GAZE TRACKING VARIATIONS USING DYNAMIC LIGHTING POSITION

CLAIM OF PRIORITY

This application claims the priority benefit of commonly-assigned U.S. provisional patent application No. 61/881,656 filed Sep. 24, 2013, the entire disclosures of which are incorporated herein by reference.

CROSS REFERENCE TO RELATED APPLICATIONS

This application is related to commonly-assigned, co-pending U.S. application Ser. No. 14/493,738, to Eric Larsen, entitled "GAZE TRACKING VARIATIONS USING LEDs", filed the same day as the present application, the entire contents of which are herein incorporated by reference.

This application is related to commonly-assigned, co-pending U.S. application Ser. No. 14/493,766, to Eric Larsen, entitled "GAZE TRACKING VARIATIONS USING VISIBLE LIGHTS OR DOTS", filed the same day as the present application, the entire contents of which are herein incorporated by reference.

FIELD

The present disclosure relates to eye gaze tracking. In particular, aspects of the present disclosure relate to light sources for optical eye gaze tracking systems.

BACKGROUND

Eye gaze tracking has use in a wide range of applications, including medical research, automobile technology, computer entertainment and video game programs, control input devices, augmented reality glasses, and more.

Some known eye gaze tracking techniques involve illuminating the eyes by emitting light from one or more light sources and detecting reflections of the emitted light off of the eyes with a sensor. Typically, this is accomplished using invisible light sources in the infrared range and capturing image data (e.g., images or video) of the illuminated eyes with an infrared sensitive camera. Image processing algorithms are then used to analyze the image data to determine eye gaze direction.

Generally, eye tracking image analysis takes advantage of characteristics distinctive to how light is reflected off of the eyes to determine eye gaze direction from the image. For example, the image may be analyzed to identify eye location based on corneal reflections in the image data, and the image may be further analyzed to determine gaze direction based on a relative location of the pupils in the image.

Two common gaze tracking techniques for determining eye gaze direction based on pupil location are known as Bright Pupil tracking and Dark Pupil tracking. Bright Pupil tracking involves illumination of the eyes with a light source that is substantially in line with the optical axis of the camera, causing the emitted light to be reflected off of the retina and back to the camera through the pupil. The pupil presents in the image as an identifiable bright spot at the location of the pupil, similar to the red eye effect which occurs in images during conventional flash photography. Dark Pupil tracking involves illumination with a light source that is substantially off line from the optical axis of the camera, causing light directed through the pupil to be reflected away from the optical axis of the camera, resulting in an identifiable dark spot in the image at the location of the pupil.

In order to effectively determine the desired eye gaze characteristics (e.g., eye position, gaze direction, and the like), these tracking techniques generally rely on the tracking system's ability to effectively illuminate the user's eyes with the light source and effectively detect the corresponding reflections of the emitted light off of these eyes. Unfortunately, in many traditional systems, environmental factors and other factors such as variable lighting conditions can interfere with the tracking system's ability to perform these functions, causing poor tracking performance and intermittent operation.

It is within this context that aspects of the present disclosure arise.

SUMMARY

An implementation of the present disclosure may include a method comprising: emitting light from an eye tracking device; capturing one or more images with the eye tracking device of an area illuminated by said emitting the light; determining one or more gaze characteristics from analysis of the images based on eye illuminations within the images from said emitting the light; analyzing the images to detect a pre-defined change in lighting conditions in the images; and triggering a change of a position of a source of the light upon detection of the pre-defined change in the light conditions. The pre-defined change may be an occurrence of glare which interferes with the eye illuminations in the images. The eye tracking device may have a plurality of light sources, wherein said emitting the light includes initially emitting the light from one or more first light sources selected from the plurality of light sources and, after said change in the position, emitting light from one or more second light sources selected from the plurality of light sources which are different from the first light sources, and wherein said triggering the change includes triggering a change from emitting the light from the first light sources to emitting light from the second light sources.

Another implementation may include a system comprising: an eye tracking device; and a computing device, wherein the system is configured to perform a method, the method comprising: emitting light from the eye tracking device; capturing one or more images with the eye tracking device of an area illuminated by said emitting the light; determining one or more gaze characteristics from analysis of the images with the computing device based on eye illuminations within the images from said emitting the light; analyzing the images with the computing device to detect a pre-defined change in lighting conditions in the images; and triggering a change with the computing device of a position of a source of the light upon detection of the pre-defined change in the light conditions.

Another implementation of the present disclosure may include a non-transitory computer readable medium having processor-executable instructions embodied therein, wherein execution of the instructions by a processor causes a processor to perform a method, the method comprising: emitting light from an eye tracking device; capturing one or more images with the eye tracking device of an area illuminated by said emitting the light; determining one or more gaze characteristics from analysis of the images based on eye illuminations within the images from said emitting the light; analyzing the images to detect a pre-defined change in lighting conditions in the images; and triggering a change of a position of a source of the light upon detection of the pre-defined change in the light conditions.

BRIEF DESCRIPTION OF THE DRAWINGS

The teachings of the present disclosure can be readily understood by considering the following detailed description in conjunction with the accompanying drawings, in which.

DETAILED DESCRIPTION

Figure 1A:
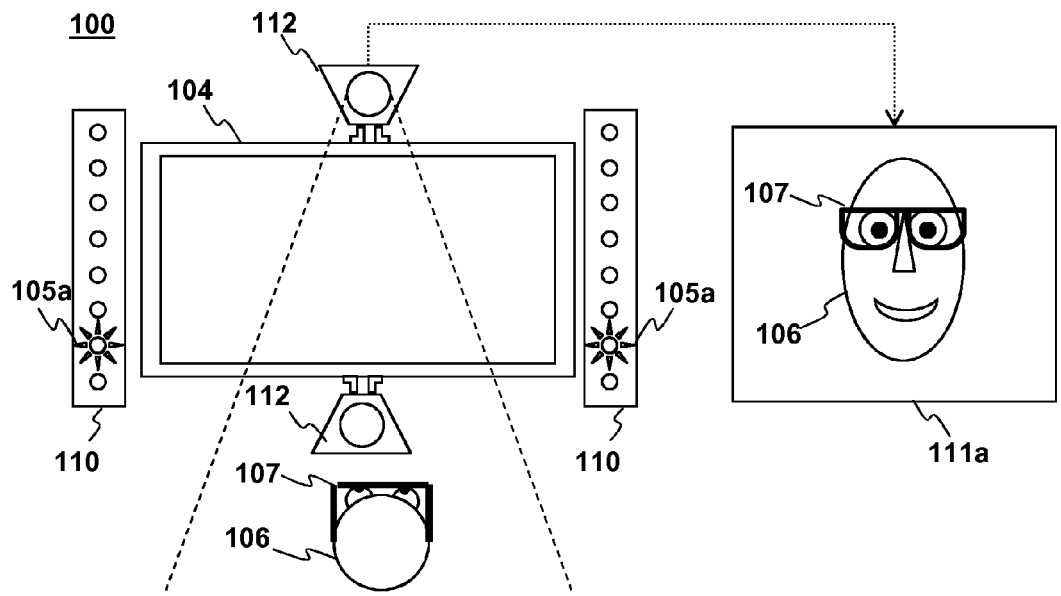
FIGS. 1A-1D is a process flow diagram depicting an eye tracking device and a method of tracking eyes with the eye tracking device to illustrate various aspects of the present disclosure

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

Introduction

Eye tracking devices may utilize a lighting source to illuminate eyes, and a camera to capture images of the illuminated eyes. The eye illuminations contained in the images may then be analyzed to determine the desired eye gaze characteristics, such as eye position, eye movements, gaze direction, gaze point, and the like. However, one challenge with such systems is that variations in lighting conditions may cause interference with the ability of the tracking system to capture images of the eye illuminations used to determine the desired gaze characteristics. For example, many people wear eyeglasses, which sometimes cause reflections that obscure the eyeglass wearer's eyes in images captured with the eye tracking device. As a user moves around or changes head position, changes in head orientation with respect to the eye tracking device may cause reflections off of the glasses which obscure the user's eyes in the images, and the eye gaze tracking may become intermittent as a result.

According to aspects of the present disclosure, variations in lighting conditions which interfere with eye tracking may be accounted for using an eye tracking device having a dynamic lighting position. As sources of interference due to lighting conditions are detected in the images, a lighting position of the eye tracking device may be changed, altering the lighting conditions for the images captured with the eye tracking device and providing clearer images of the eye illuminations that may analyzed to determine gaze characteristics.

Implementation Details

An illustrative process flow of an example system 100 and method of eye tracking is depicted in FIGS. 1A-1D. In the implementation depicted in FIGS. 1A-1D, an eye tracking device having a dynamic lighting position is used to illuminate eyes and capture images of the illuminated eyes.

The images may be analyzed to determine one or more gaze characteristics of the eyes, and the position of the lighting may change during the illumination based upon analysis of the images.

As shown in FIG. 1A-1D, the example system 100 may include an eye tracking device having a dynamic lighting source 110 and a camera 112 which is sensitive to light emitted from the lighting source 110. By way of example, and not by way of limitation, the light emitted from the dynamic lighting source 110 may be invisible light such as infrared light, and the camera 112 may be an infrared sensitive camera. The system 100 may also include a display device 104 which may operate in coordination with the eye tracking device for various eye tracking applications, e.g., to determine a user's gaze point on the screen. The camera 112 may be located above the display device 104 or below the display device. It may be advantageous to locate the camera 112 above the display device, since eyes tend to be less obscured when viewed from below eye level.

In order to perform eye tracking, the system 100 may emit light from the dynamic lighting source 110 and capture images 111a-d of an area illuminated by light with the camera 112 of the eye tracking device. The images 111a-d may contain images of a user 106, whose face and eyes are illuminated by the emitted light, and the images may 111a-d may be analyzed by a computing device (not separately pictured) which may process the images to determine one or more characteristics of the eye gaze of the user 106 based on analysis of the illuminations of the user's eyes. In one implementation, this may involve analyzing the images 111a-d to identify eye illuminations, including corneal reflections caused by the emitted light and/or one or more Dark Pupils (i.e. a dark spot at a pupil location of an eye illuminated by light that is off-axis from the camera 112). These characteristic eye illuminations in the images 111a-d may be analyzed to determine the desired gaze characteristics, such as eye position, eye movements, gaze direction, gaze point, and the like, using suitable image processing algorithms processed with the computing device.

As shown in FIG. 1A, the light from the dynamic lighting source 110 may be initially emitted from one or more initial positions 105a. In the example illustrated in FIG. 1A, the initial light source position 105a includes a plurality of light sources horizontally offset from one another at an initial vertical position, and the dynamic lighting source 110 includes a plurality of discrete light sources disposed at different locations. The eye tracking device may capture images 111a of the illuminated user 106 with the camera 112 of the eye tracking device, and the user may have an initial head orientation and eye gaze direction as shown in FIG. 1A.

Figure 1B:
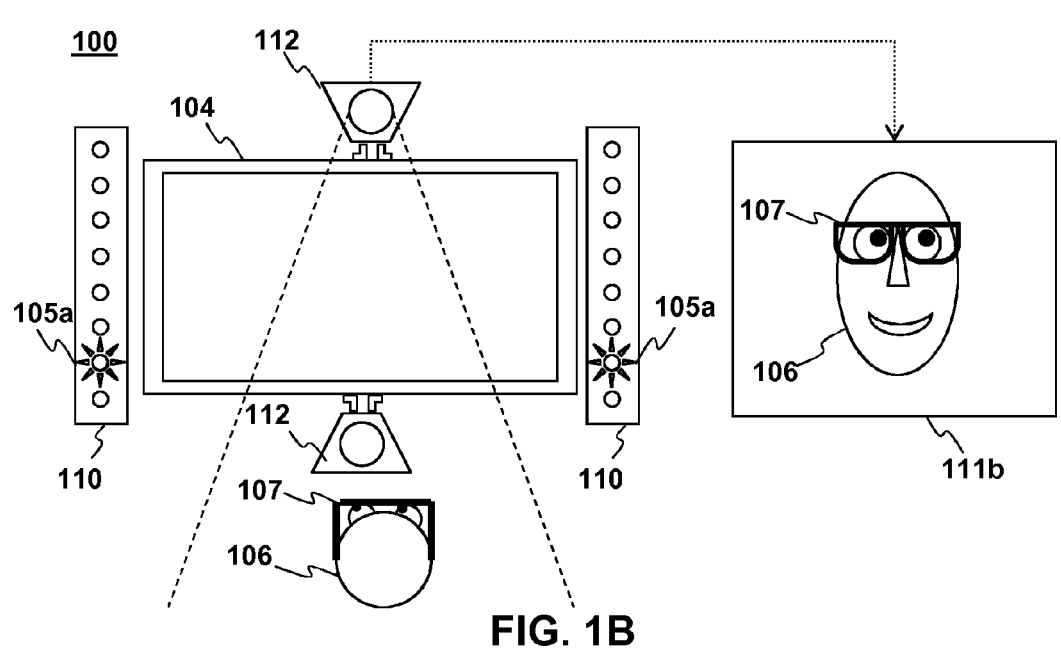

As shown in FIG. 1B, the system 100 may continue to track the eyes of the user 106, and the images 111b of the user 106 depict a user having a changed eye gaze direction. By way of example, the image 111b depicted in FIG. 1B may include a Dark Pupil at a different location from a Dark Pupil in the image 111a in FIG. 1A, and this Dark Pupil may be analyzed to determine a gaze direction of the user 106 based on the location of this Dark Pupil. Moreover, as illustrated in FIG. 1B, the images 111b of the user 106 are clear and generally free from interfering lighting conditions which interfere with the capture of the eye illuminations. For example, while the user 106 is wearing eyeglasses 107, a clear image of the user's illuminated eyes is still captured by the camera 112 through the glasses 107. Accordingly, the initial source position 105a of the emitted light may be maintained.

Figure 1C:
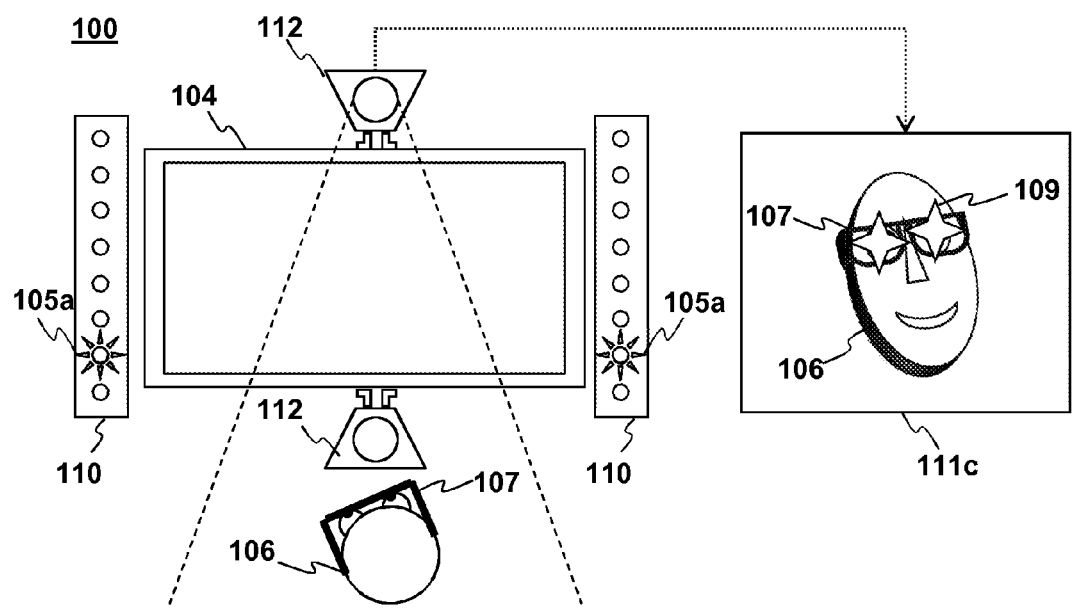

Turning to FIG. 1C, the head orientation of the user 106 has changed relative to the system 100. In particular, the user's head orientation relative to the lighting source 110 and the camera 112 has changed. As a result of the orientation of the user's eyeglasses 107 relative to the components 110, 112 of the eye tracking device, light emitted from the initial lighting position 105a causes glare 109 from the user's eyeglasses due to reflections of the emitted light off of the glasses. As a result, in the image 111c of the user, the user's eyes are obscured by the glare 109, and the system 100 may be unable to determine the desired gaze characteristics from analysis the eye illuminations. For example, this glare may obscure a dark spot (i.e. Dark Pupil) in the images at a location of the eyes that is used to determine gaze direction. The changed lighting conditions present in FIG. 1C may interfere with tracking data gathered by the system 100, causing the tracking to become intermittent.

Figure 1D:
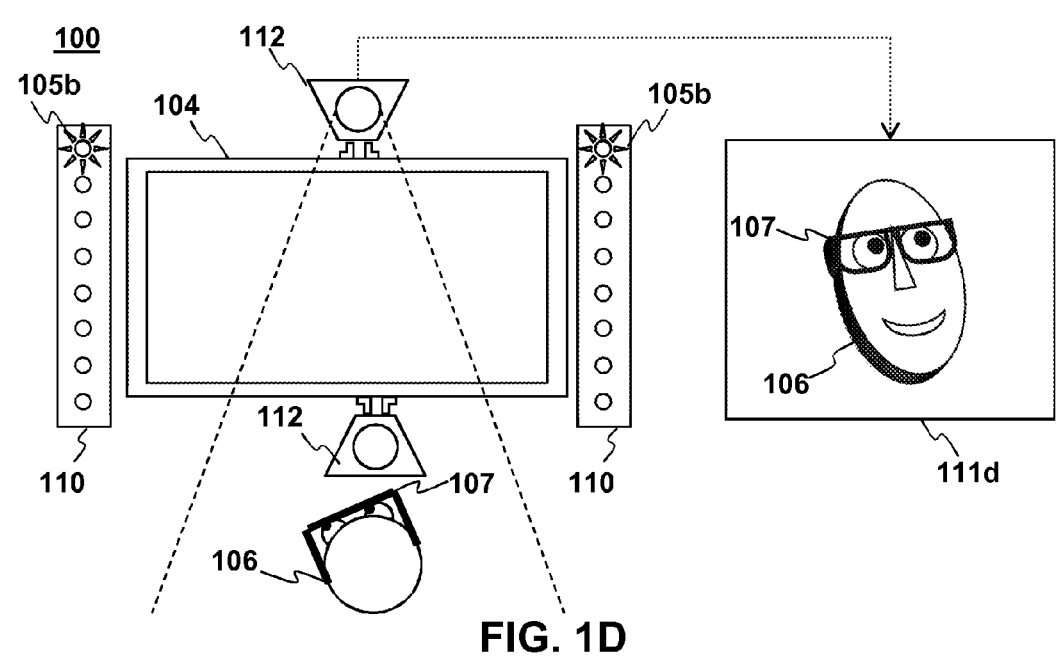

As shown in FIG. 1D, upon occurrence of these changed lighting conditions, the source position of the lighting may change to a new position 105b in order to account for the changed lighting conditions. As a result, as shown in the image 111d in FIG. 1D, the glare from the user's glasses 107 is removed due to the change in position of the lighting source 110, and a clearer image of the user's eyes is obtained. By way of example, a Dark Pupil in the image 111c may be identifiable by the system 100 and not obscured by glare, even though the user's head orientation with respect to the remaining components of the system 100 is unchanged.

In one implementation of the present disclosure, the change in lighting position depicted in FIG. 1D may be triggered automatically by the system 100 and may occur virtually instantaneously, e.g. by using programming or a suitable configuration of a computing device coupled to the dynamic lighting source 110. By way of example, the computing device may continuously analyze the one or more images captured by the camera 112, which may be a plurality of still images or a video in the form of a "moving image", in order to detect a pre-defined change in the light conditions of the tracking environment. For example, the system may detect that glare is present in the images in a location that interferes with image capture of the eye illuminations, or the analysis may be used to detect some other change which caused the tracking performance to degrade or become intermittent. Upon detecting these conditions the system may automatically send a control signal to the dynamic lighting source 110, which causes the position to change to new position 105b. The net affect may be a system which dynamically adjusts the lighting position in real-time as lighting conditions change in the captured images, minimizing or preventing any intermittence in the eye gaze tracking and/or otherwise improving tracking performance.

In the example depicted in FIGS. 1A-1D, the dynamic lighting source 110 is depicted as a plurality of discrete light sources, such as infrared LEDs which each emit invisible light, and the different light sources are each fixed in a different location in the illustrated implementation. More specifically, the dynamic light source 110 in the illustration of FIG. 1D is depicted as a plurality of sets of light sources, with each of the sets having a plurality of light sources offset from each other in a vertical direction. In FIGS. 1A-1D, the plurality of sets is arranged as two vertical bars disposed on opposing sides of a display device 104, and each of the vertical bars has a plurality of light sources arranged in a line, and, as shown in FIG. 1D, the lighting position may be moved in a vertical direction up and down, e.g., by selectively turning off and on various ones of the light sources based on present lighting conditions detecting from analysis of the images 111a-d.

It will be readily understood that a dynamic lighting source in accordance with aspects of the present disclosure may be arranged in a variety of different implementations having a variety of different configurations. For example, the plurality of light sources depicted in FIGS. 1A-1D may be configured in any of a variety of geometric orientations, and any arbitrary number of discrete light sources or different light sources positions may be used. In one implementation, different light sources within a set may be offset from each other in a vertical direction, offset in a horizontal direction, or offset in both horizontal and vertical directions, such as by having a diagonal layout or curved configuration. For example, they may be arranged in a fully or partially circular or elliptical configuration around the display device, or around the camera, or in some other location, in which case they would be offset from each other in both a horizontal and vertical directions due to the curvature. In another example, some or all of the light sources may be arranged behind the display device 104, in which case the display device may be configured to transmit whatever wavelength of light is emitted by the light sources.

By way of further example, it may be possible to use some motorized or other electronically movable lighting source in order to change the position of the light source used to illuminate the user's eyes. In yet another example, an optical system involving steerable mirrors or some type of optical switching system may change the light source position in accordance with various aspect described herein.

Likewise, the system may be configured to change lighting positions multiple times before settling on a current position in order to determine an optimal light source position that accounts for the present light conditions. Furthermore, whatever configuration is used, the system may be calibrated to account for the changes in light position by processing the images based on the present light source location. An example of a calibration method which may be used in implementations of the present disclosure is describe in U.S. application Ser. No. 14/493,766, to Eric Larsen, entitled "GAZE TRACKING VARIATIONS USING VISIBLE LIGHTS OR DOTS", filed the same day as the present application, the entire contents of which are herein incorporated by reference. In another example, some or all of the components may be built into a common device, such a display device including the plurality of light sources or other variable lighting fixed in its casing.

It is further noted that in the example depicted in FIGS. 1A-1D, the camera 112 is stationary during the eye tracking while the light source position is dynamic. As a result, the light source position relative to the camera may changes as the position is adjusted in real-time to account for the changes lighting conditions. Therefore, it may be preferred to utilize Dark Pupil tracking so that a plurality of different light source positions which are off-set from the optical axis of the camera 112 may be used in order to affect the direction from which the illumination originates to a significant enough degree, without having to keep the camera in-line with the optical axis for a Bright Pupil tracking system. However, it is noted that it may be possible to use a Bright Pupil tracking system with a dynamic lighting position in accordance with aspects of the present disclosure. For example, a system having a dynamic camera position coordinated with the dynamic lighting position may be used in an alternative implementation of the present disclosure, such as a system with multiple cameras.

It is further noted that other features may be included in the example system 100. By way of example, the lighting source 110 may include pulsed lighting in the form of pulsed LEDs in order to filter out environmental lighting (e.g., due to environmental infrared radiation sources such as the sun). The system 100 may be configured to process only the eye illuminations that are in pulsed in coordination with the emitted signal in order to filter out the environmental lighting, e.g., as a way of pulse coding the light signal emitted from the lighting source 110 of the tracking device. By way of further example, the camera 112 may use a global shutter that is timed in sync with the LEDs of the lighting source 110. The LEDs may be controlled to illuminate only when the shutter is open, allowing for a brighter LED signal that would be brighter than environmental light during the time that the shutter is open.

Figure 2:
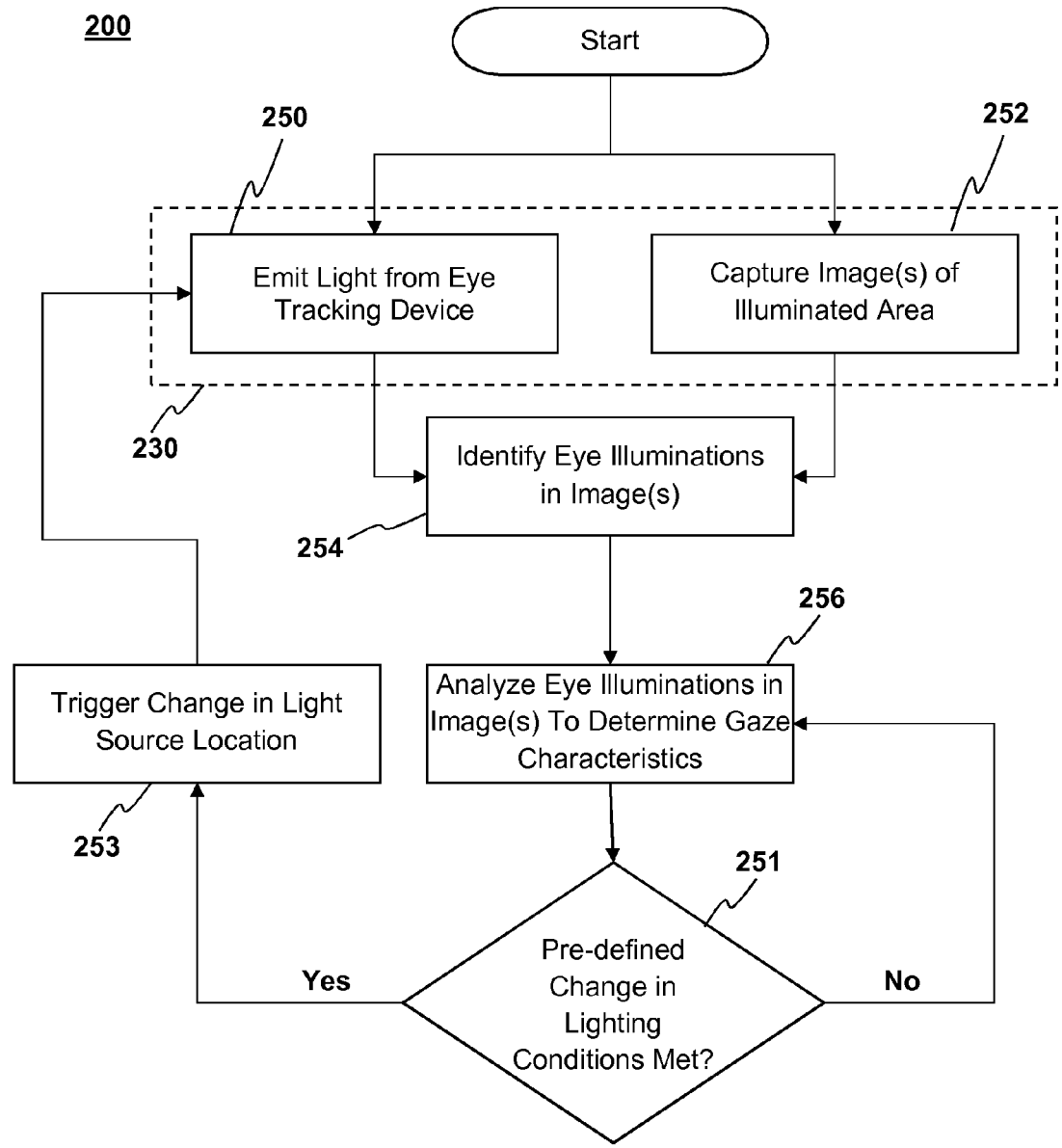
FIG. 2 is a flow diagram depicting an example method of eye tracking to illustrate various aspects of the present disclosure.

An example of an eye tracking method 200 using dynamic lighting is depicted in FIG. 2 to illustrate various aspects of the present disclosure. In implementations of the present disclosure, some or all of the example method 200 may be performed by a computing device coupled to an eye tracking device which is configured to illuminate eyes using variable lighting, such as the example system 100 depicted in FIGS. 1A-1D.

The example method 200 includes gathering eye tracking data 230 with an eye tracking device, which may include emitting light from a light source 250 (e.g. infrared light) of the eye tracking device and detecting an area illuminated by the emitted light 252 (e.g. by capturing one or more infrared images of the illuminated area). The images may be processed to identify eye illuminations in the images 254 of one or more eyes illuminated by the emitted light, e.g., by identifying a face and/or by identifying corneal reflections of the emitted light in the images. Processing of the images may be performed, e.g., by a computing device coupled to a camera of the eye tracking device and which is configured to process the eye tracking data.

The eye illuminations identified in the images may be analyzed by the computing device to determine one or more gaze characteristics 256, such as eye position, eye movements, gaze direction, gaze point, etc., or some combination thereof. By way of example, this may be performed using a Dark Pupil image processing technique in which a dark spot at the location of the eye illuminations that is indicative of a pupil location is analyzed to determine a relative direction of the gaze of a user. By way of further example, this may involve determining a gaze point or a point of regard on a display device from analysis of the eye illuminations, such as the display device 104 of FIGS. 1A-1D.

The images captured by the eye tracking device may also be analyzed, e.g. periodically or continuously while the eyes are being tracked 256, to detect a change in lighting conditions 251 which interferes with image capture of the eye illuminations. In one implementation, this may involve analyzing the images to detect a presence of a glare which interferes with the eye illuminations based upon pre-defined parameters that indicate a presence of the glare. By way of example, this may involve analyzing an area of the images which corresponds with a Dark Pupil to detect a presence of a bright spot. When the analysis detects that this bright spot is present, or when a size and/or intensity of such a bright spot exceeds some pre-defined threshold, this may indicate that the pre-defined change in lighting conditions 251 has been met. For example, such a bright spot may indicate that glare from a user's eyeglasses is obscuring the eye illuminations being used to determine the gaze characteristics 256.

Upon determining that the pre-defined change in light conditions has been met, the computing device may trigger a change in a source location 253 of the emission of light 250 from the eye tracking device, e.g., as shown and described in FIGS. 1C-1D above. By way of example, the computing device may be in communication with a dynamic light source of the eye tracking device, and the computing device may send a control signal that changes a position of the light. In one example, this may involve turning off one or more LEDs and turning on one or more differently located LEDs, thereby causing the light to illuminate the eye from a different location and potentially improving the lighting conditions contained in the images for eye gaze tracking. If the change in light conditions has not occurred, as determined at 251, the method may continue to analyze the images as normal, with no change in the light source location. By way of example, this operation depicted in the example method 200 may be performed continuously during the eye tracking in real-time in order to dynamically adjust the lighting position on the fly.

Figure 3:
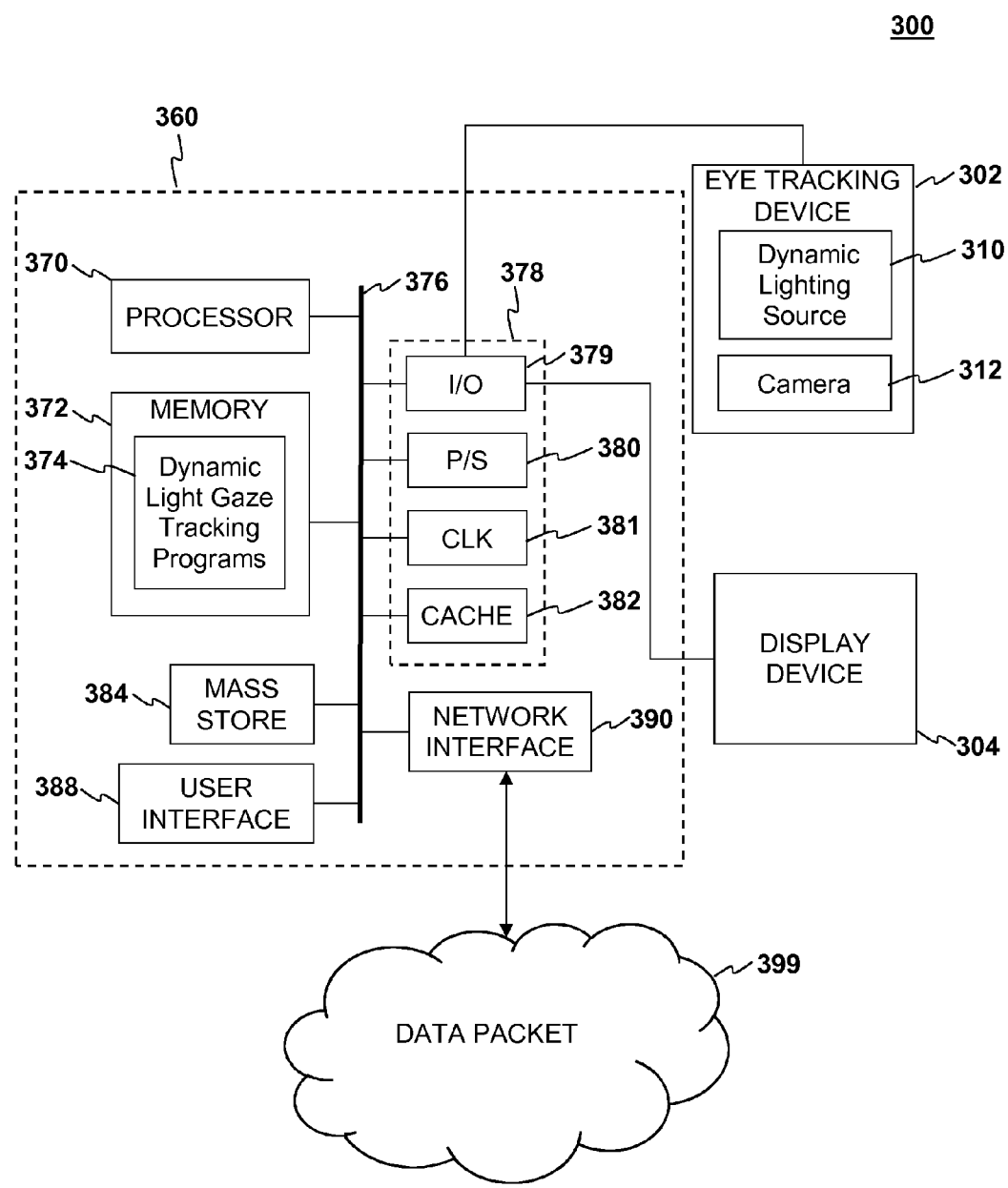
FIG. 3 is a block diagram depicting an example of a system for eye tracking to illustrate various aspects of the present disclosure.

FIG. 3 depicts an example system for eye tracking 300 to further illustrate various aspects of the present disclosure. The example system 300 may include a computing device 360 which is coupled to an eye tracking device 302 and a display device 304 in order to perform eye gaze tracking and/or calibration for eye tracking in accordance with aspects of the present disclosure. The display device 386 may be in the form of a cathode ray tube (CRT), flat panel screen, touch screen, or other device that displays text, numerals, graphical symbols, or other visual objects. According to aspects of the present disclosure, the computing device 360 may be an embedded system, mobile phone, personal computer, tablet computer, portable game device, workstation, game console, and the like. Moreover, the computing device 360, the eye tracking device 302, the display device 304, or any combination thereof may form an integral unit or be implemented as separate components which may be in communication with each other.

The eye tracking device 302 may be coupled to the computing device 360, and may include a dynamic lighting source 310 similar to light sources 110 of FIGS. 1A-1D. By way of example, and not by way of limitation, the lighting source 310 may be an invisible lighting source in the form of one or more infrared LEDs, which may be configured to illuminate a user's eyes in order to gather eye tracking data with the sensor 312, and which may have a position which is electronically controllable to different positions, e.g., as shown in FIGS. 1A-1D. The sensor 312 of the eye tracking device may be a detector which is sensitive to light emitted from the light source 310. For example, the sensor 312 may be a camera sensitive to the light source such as an infrared camera, and the camera 312 may be positioned relative to the eye tracking device and the lighting source so that it may capture images of an area illuminated by the lighting source 310.

The computing device 360 may be configured to operate in coordination with the eye tracking device 302 and the display device 304, in order to perform eye gaze tracking and determine lighting conditions in accordance with aspects of the present disclosure. The computing device 360 may include one or more processor units 370, which may be configured according to well-known architectures, such as, e.g., single-core, dual-core, quad-core, multi-core, processor-coprocessor, cell processor, and the like. The computing device 360 may also include one or more memory units 372

(e.g., random access memory (RAM), dynamic random access memory (DRAM), read-only memory (ROM), and the like).

The processor unit 370 may execute one or more programs, portions of which may be stored in the memory 372, and the processor 370 may be operatively coupled to the memory 372, e.g., by accessing the memory via a data bus 376. The programs may be configured to perform eye gaze tracking and determine lighting conditions for the system 300. By way of example, and not by way of limitation, the programs may include dynamic lighting source gaze tracking programs 374, execution of which may cause the system 300 to perform a method having one or more features in common with the method of FIG. 2. By way of example, and not by way of limitation, the gaze tracking programs 374 may include processor executable instructions which cause the system 300 to determine one or more gaze tracking parameters of the system 300 from eye tracking data gathered with the camera 312 while light is emitted from the dynamic lighting source 310. The gaze tracking programs 374 may also include instructions which analyze images gathered with the camera 312 in order to detect a presence of a change in lighting conditions, e.g., as described above with respect to FIG. 2.

The computing device 360 may also include well-known support circuits 378, such as input/output (I/O) circuits 379, power supplies (P/S) 380, a clock (CLK) 381, and cache 382, which may communicate with other components of the system, e.g., via the bus 376. The computing device 360 may optionally include a mass storage device 384 such as a disk drive, CD-ROM drive, tape drive, flash memory, or the like, and the mass storage device 384 may store programs and/or data. The computing device 360 may also include a user interface 388 to facilitate interaction between the system 300 and a user. The user interface 388 may include a keyboard, mouse, light pen, game control pad, touch interface, or other device.

The system 300 may also include a controller (not pictured) which interfaces with the eye tracking device 302 in order to control the source position of the lighting source 310 based on the image analysis of the gaze tracking programs 374. The system 300 may also execute one or more general computer applications (not pictured), such as a video game, which may incorporate aspects of eye gaze tracking as sensed by the tracking device 302 and processed by the tracking programs 374.

The computing device 360 may include a network interface 390, configured to enable the use of Wi-Fi, an Ethernet port, or other communication methods. The network interface 390 may incorporate suitable hardware, software, firmware or some combination thereof to facilitate communication via a telecommunications network. The network interface 390 may be configured to implement wired or wireless communication over local area networks and wide area networks such as the Internet. The computing device 360 may send and receive data and/or requests for files via one or more data packets 399 over a network.

It will readily be appreciated that variations on the components depicted in FIG. 3 are possible, and that various ones of these components may be implemented in hardware, software, firmware, or some combination thereof. For example, the some features or all features of the calibration programs contained in the memory 372 and executed by the processor 370 may instead be implemented via suitably configured hardware, such as one or more application specific integrated circuits (ASIC).

CONCLUSION

It is noted that aspects of the present disclosure have been described with reference to eye tracking devices that use infrared light sources, which has developed as a relatively standard light source for optical eye tracking techniques. However, it is understood that other implementations are possible. For example, in implementations of the present disclosure, other invisible light sources are possible, such as ultraviolet light. By way of further example, in implementations of the present disclosure, visible light sources are possible for eye illumination, although it may be desirable to use invisible light sources in order to avoid distracting a user.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature described herein, whether preferred or not, may be combined with any other feature described herein, whether preferred or not. In the claims that follow, the indefinite article "a", or "an" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A method comprising:
    emitting light from an eye tracking device;
    capturing one or more images with the eye tracking device of an area illuminated by said emitting the light;
    determining one or more gaze characteristics from analysis of the images based on eye illuminations within the images from said emitting the light;
    analyzing the images to detect a pre-defined change in lighting conditions in the images; and
    triggering a change of a position of a source of the light upon detection of the pre-defined change in the light conditions.

2. The method of claim 1, wherein the pre-defined change is an occurrence of glare which interferes with the eye illuminations in the images.

3. The method of claim 1, wherein said determining the gaze characteristics based on the eye illuminations includes analyzing a Dark Pupil in the images which is generated by said emitting the light, wherein said analyzing the images to detect the pre-defined change in lighting conditions includes analyzing a location of the Dark Pupil for a bright spot at the location which exceeds a pre-defined size threshold, a pre-defined intensity threshold, or a combination thereof.

4. The method of claim 1,
    wherein the eye tracking device has a plurality of light sources,
    wherein said emitting the light includes initially emitting the light from one or more first light sources selected from the plurality of light sources and, after said change in the position, emitting light from one or more second light sources selected from the plurality of light sources which are different from the first light sources, and wherein said triggering the change includes triggering a change from emitting the light from the first light sources to emitting light from the second light sources.

5. The method of claim 4, wherein the plurality of light sources are infrared LEDs, wherein the images are infrared images, and wherein triggering the change includes turning off the first infrared LEDs and turning on the second infrared LEDs.

6. The method of claim 4, wherein the second light sources are offset from the first light sources in a vertical direction.

7. The method of claim 4, wherein the pre-defined change is an occurrence of glare which interferes with the eye illuminations in the images.

8. The method of claim 1, wherein said determining the gaze characteristics includes determining a gaze direction.

9. A system comprising:
an eye tracking device; and
a computing device, wherein the system is configured to perform a method, the method comprising:
emitting light from the eye tracking device;
capturing one or more images with the eye tracking device of an area illuminated by said emitting the light;
determining one or more gaze characteristics from analysis of the images with the computing device based on eye illuminations within the images from said emitting the light;
analyzing the images with the computing device to detect a pre-defined change in lighting conditions in the images; and
triggering a change with the computing device of a position of a source of the light upon detection of the pre-defined change in the light conditions.

10. The system of claim 9,
wherein the eye tracking device has a plurality of light sources,
wherein said emitting the light includes initially emitting the light from one or more first light sources selected from the plurality of light sources and, after said change in the position, emitting light from one or more second light sources selected from the plurality of light sources which are different from the first light sources, and
wherein said triggering the change includes triggering a change from emitting the light from the first light sources to emitting light from the second light sources.

11. The system 10, The method of claim 4, wherein the plurality of light sources are infrared LEDs, wherein the images are infrared images, and wherein triggering the change includes turning off the first infrared LEDs and turning on the second infrared LEDs.

12. The system of claim 10, wherein the pre-defined change is an occurrence of glare which interferes with the eye illuminations in the images.

13. The system of claim 9,
wherein the eye tracking device has one or more sets of light sources,
wherein each said set has a plurality of light sources offset in a vertical direction with respect to each other,
wherein said emitting the light includes initially emitting the light from one or more first light sources selected from each of the sets of the light sources and, after said change in the position, emitting light from one or more second light sources selected from each of the sets of the light sources which are different from the first light sources, and
wherein said triggering the change includes triggering a change from emitting the light from the first light sources to emitting light from the second light sources.

14. The system of claim 13, wherein the one or more sets are a plurality of sets of light sources, wherein each of the plurality of the sets are horizontally offset from each other.

15. The system of claim 9, wherein the pre-defined change is an occurrence of glare which interferes with the eye illuminations in the images.

16. The system of claim 9, wherein said determining the gaze characteristics based on the eye illuminations includes analyzing a Dark Pupil in the images which is generated by said emitting the light, wherein said analyzing the images to detect the pre-defined change in lighting conditions includes analyzing a location of the Dark Pupil for a bright spot at the location which exceeds a pre-defined size threshold, a pre-defined intensity threshold, or a combination thereof.

17. The system of claim 9, wherein said determining the gaze characteristics includes determining a gaze direction.

18. A non-transitory computer readable medium having processor-executable instructions embodied therein, wherein execution of the instructions by a processor causes a processor to perform a method, the method comprising:
emitting light from an eye tracking device;
capturing one or more images with the eye tracking device of an area illuminated by said emitting the light;
determining one or more gaze characteristics from analysis of the images based on eye illuminations within the images from said emitting the light;
analyzing the images to detect a pre-defined change in lighting conditions in the images; and
triggering a change of a position of a source of the light upon detection of the pre-defined change in the light conditions.

19. The non-transitory computer readable medium of claim 18, wherein the pre-defined change is an occurrence of glare which interferes with the eye illuminations in the images.

20. The non-transitory computer readable medium of claim 18,
wherein the pre-defined change is an occurrence of glare which interferes with the eye illuminations in the images,
wherein the eye tracking device has a plurality of light sources,
wherein said emitting the light includes initially emitting the light from one or more first light sources selected from the plurality of light sources and, after said change in the position, emitting light from one or more second light sources selected from the plurality of light sources which are different from the first light sources, and
wherein said triggering the change includes triggering a change from emitting the light from the first light sources to emitting light from the second light sources.

* * * * *